(12) United States Patent
Yoshikawa

(10) Patent No.: US 7,956,222 B2
(45) Date of Patent: Jun. 7, 2011

(54) METHODS FOR PRODUCING DIBROMOFLUOROBENZENE DERIVATIVES

(75) Inventor: Seiji Yoshikawa, Kashima-gun (JP)

(73) Assignee: Eisai R&D Management Co., Ltd (JP)

( * ) Notice: Subject to any disclaimer, the term of this patent is extended or adjusted under 35 U.S.C. 154(b) by 642 days.

(21) Appl. No.: 11/573,882

(22) PCT Filed: Jul. 27, 2005

(86) PCT No.: PCT/JP2005/013692
§ 371 (c)(1),
(2), (4) Date: Aug. 3, 2007

(87) PCT Pub. No.: WO2006/018954
PCT Pub. Date: Feb. 23, 2006

(65) Prior Publication Data
US 2008/0045753 A1 Feb. 21, 2008

(30) Foreign Application Priority Data
Aug. 17, 2004 (JP) ................. 2004-237181

(51) Int. Cl.
*C07C 41/22* (2006.01)
(52) U.S. Cl. ..................................... 568/649
(58) Field of Classification Search ........... None
See application file for complete search history.

(56) References Cited

U.S. PATENT DOCUMENTS

| 4,435,601 | A * | 3/1984 | Formanek et al. | ............ 568/430 |
| 7,244,730 | B2 * | 7/2007 | Suzuki et al. | ............... 514/235.2 |
| 2005/0004204 | A1 | 1/2005 | Suzuki et al. | |
| 2006/0058370 | A1 | 3/2006 | Shimomura et al. | |
| 2008/0214834 | A1 | 9/2008 | Yoshizawa et al. | |

FOREIGN PATENT DOCUMENTS

| WO | WO 02/85855 A1 | 10/2002 |
| WO | WO 2004/078721 A1 | 9/2004 |
| WO | WO 2006/050843 A1 | 5/2006 |

OTHER PUBLICATIONS

Suzuki et al., Formylation of Phenols with Electron-withdrawing Groups in Strong Acids. Synthesis of Substituted Salicyladehydes, Chem. Pharm. Bull. vol. 31, No. 5, pp. 1751-1753, May 1983.*

* cited by examiner

*Primary Examiner* — Rosalynd Keys
(74) *Attorney, Agent, or Firm* — Kilpatrick Townsend & Stockton LLP.

(57) ABSTRACT

Methods of the present invention for producing dibromofluorobenzene derivatives (compounds II) comprise Step 1, in which compounds (I) having the following general formula (I):

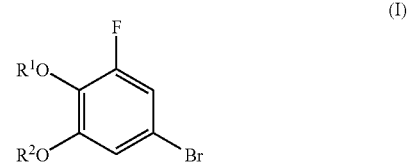

(I)

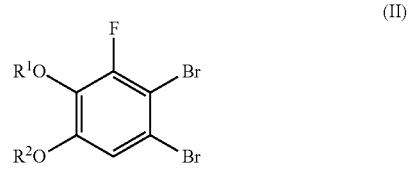

(II)

(wherein, $R^1$ and $R^2$ each independently represent a $C_{1-6}$ alkyl group) are reacted in a solvent with a brominating reagent.

7 Claims, No Drawings

METHODS FOR PRODUCING DIBROMOFLUOROBENZENE DERIVATIVES

This application is a U.S. National Phase of PCT/JP2005/013692, filed Jul. 27, 2005, which claims priority to Japanese Patent Application No. 2004-237181, filed Aug. 17, 2004. The contents of all of the aforementioned applications are herein incorporated by reference in their entirety.

TECHNICAL FIELD

The present invention relates to methods for producing dibromofluorobenzene derivatives. The invention also relates to monobromofluorobenzene derivatives.

BACKGROUND ART

One example of an antithrombosis approach is a method that inhibits the enzyme activity of thrombin. Compounds having an antagonistic effect on thrombin receptors are recently anticipated to exert a prominent effect in the treatment and prevention of diseases in which thrombin is involved, for example, thrombosis, vascular restenosis, deep venous thrombosis, pulmonary embolism, cerebral infarction, heart diseases, disseminated intravascular coagulation syndrome, hypertension, inflammatory diseases, rheumatism, asthma, glomerulonephritis, osteoporosis, neurological disorders, and malignant tumors. Therefore, thrombin receptor antagonists that satisfy points such as pharmacological activity, specificity for thrombin receptors, safety, dose, and oral effectiveness are needed.

2-Iminopyrrolidine derivatives and salts thereof have already been found to have a prominent inhibitory activity on thrombin receptors and to be useful as thrombin receptor antagonists (Patent Document 1). Among the 2-iminopyrrolidine derivatives and salts thereof, Patent Document 1 describes methods for producing, for example, compounds having the following general formula (A1):

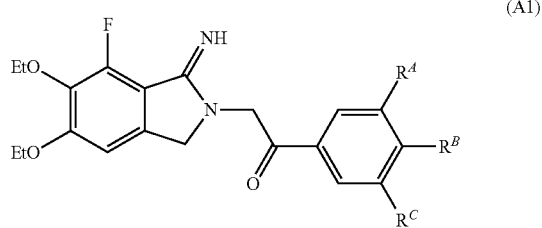

(wherein $R^A$ represents a $C_{1-6}$ alkyl group, $R^B$ represents a $C_{1-6}$ alkoxy group, and $R^C$ represents a 5-14 membered heterocyclic group), or salts thereof.

The aforementioned Patent Document 1 describes that fluorine-containing cyclic benzamidine derivatives (A2) having the following formula

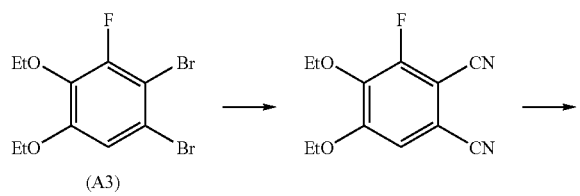

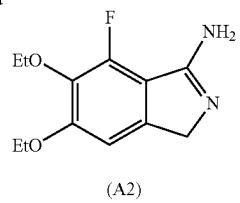

may be important intermediates in the production of the aforementioned compounds A1, and further describes a method for producing fluorine-containing cyclic benzamidine derivatives (A2) using dibromofluorobenzene derivatives (A3) (Example 7 of Patent Document 1 and the like).

As a method for producing the dibromofluorobenzene derivatives (A3), the following method, for example, is disclosed (Patent Document 1, Example 7 and the like). Unless otherwise specified, "Et" represents an ethyl group in the present description.

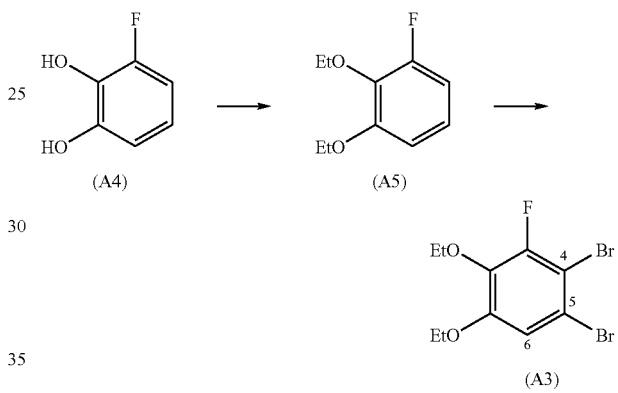

[Patent Document 1] WO 02/085855

DISCLOSURE OF THE INVENTION

Problems to be Solved by the Invention

However, the method of producing dibromofluorobenzene derivatives (A3) via compounds (A5) using the aforementioned compounds (A4) as starting materials was problematic in that byproducts were produced when obtaining (A3) from (A5), complicating the purification. For example, in the bromination reaction of compounds A5, iso-dibromo products that had been brominated at the 4- and 6-positions of the benzene ring and tribromo products that had been brominated at the 4-, 5-, and 6-positions were produced, and the dibromo products of interest (the compounds A3 above) could not be highly selectively obtained.

Therefore, convenient methods for producing dibromofluorobenzene derivatives (compounds A3) with a high total yield and a high regioselectivity for the functional groups, and which use easily available starting compounds were long anticipated.

Therefore, an object of the present invention is to provide useful methods for producing dibromofluorobenzene derivatives.

Means to Solve the Problems

The present inventor conducted dedicated research to solve the above-mentioned problems. As a result, he found that the dibromofluorobenzene derivatives of interest can be produced with a high regioselectivity by brominating compounds having the following general formula (I):

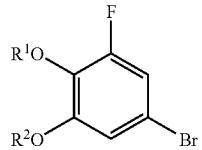
(I)

(wherein $R^1$ and $R^2$ each independently represent a $C_{1-6}$ alkyl group), which led to the completion of the present invention.

Therefore, the present invention comprises the following:

[1] a method for producing a dibromofluorobenzene derivative (compound (II)) having the following general formula (II):

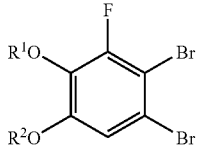
(II)

(wherein $R^1$ and $R^2$ each independently represent a $C_{1-6}$ alkyl group), wherein the method comprises the step of reacting, in a solvent, a compound (I) having the following general formula (I):

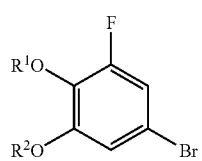
(I)

(wherein $R^1$ and $R^2$ each have the same meaning as $R^1$ and $R^2$ in the aforementioned formula (II)) with a brominating reagent (Step 1);

[2] the method of [1], wherein the brominating reagent is bromine;

[3] the method of [1] or [2], further comprising a step of reacting, in a solvent, a compound (III) having the following formula (III):

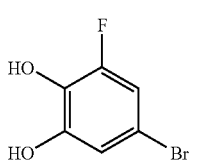
(III)

with an alkylating agent in the presence of a base to obtain the aforementioned compound (I) having the following general formula (I):

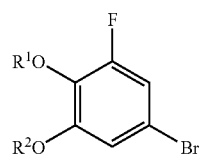
(I)

(wherein $R^1$ and $R^2$ each independently represent a $C_{1-6}$ alkyl group) (Step 2);

[4] the method of [3], wherein the alkylating agent is an alkyl halide;

[5] the method of [3] or [4], further comprising a step of reacting, in a solvent, a compound (IV) having the following formula (IV):

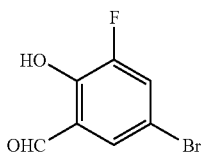
(IV)

with a peracid in the presence of a base to obtain the aforementioned compound (III) having the following formula (III):

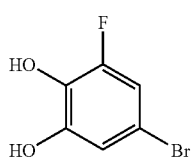
(III)

(Step 3);

[6] the method of [5], wherein the peracid is a hydrogen peroxide solution;

[7] the method of [5] or [6], further comprising a step of reacting, in a solvent, a compound (V) having the following formula (V):

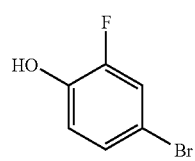
(V)

with hexamethylenetetramine to obtain the aforementioned compound (IV) having the following formula (IV):

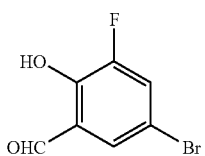
(IV)

(Step 4);
[8] the method of [1] or [3], wherein $R^1$ and $R^2$ in the aforementioned general formulae (I) and (II) are both an ethyl group;
[9] a compound having the following general formula (I):

(I)

$R^1O$ — [benzene ring with F at top, $R^2O$ at adjacent position, Br at para position]

(wherein $R^1$ and $R^2$ each independently represent a $C_{1-6}$ alkyl group);
[10] the compound of [9], wherein $R^1$ and $R^2$ are both an ethyl group;
[11] a compound having the following formula (III):

(III)

HO — [benzene ring with F, HO, Br]; and

[12] a compound having the following general formula (III-1);

(III-1)

$R^aO$ — [benzene ring with F, $R^bO$, Br]

(wherein $R^a$ and $R^b$ each independently represent a hydroxy protecting group or $R^a$ and $R^b$ together represent a protecting group (however, excluding the case where $R^a$ is a methyl group and $R^b$ is a t-butyldiphenylsilyl group)).

Effects of the Invention

According to the present invention, specific dibromofluorobenzene derivatives can be produced with a high total yield and a high regioselectivity for functional groups from easily available starting compounds.

BEST MODE FOR CARRYING OUT THE INVENTION

Step 1

$R^1O$ — [benzene ring with F, $R^2O$, Br] (I) → $R^1O$ — [benzene ring with F, Br, $R^2O$, Br] (II)

The method for producing dibromofluorobenzene derivatives (compounds (II)) of the present invention having the above general formula (II) comprises the step of reacting, in a solvent, compounds (I) having the above general formula (I) with a brominating reagent (Step 1).

In the above formula, $R^1$ and $R^2$ each independently represent a $C_{1-6}$ alkyl group.

The term "$C_{1-6}$ alkyl group" refers to a linear or branched alkyl group of one to six carbons, which is a monovalent group induced by removing any one of the hydrogen atoms from an aliphatic hydrocarbon of one to six carbons.

Specifically, the $C_{1-6}$ alkyl group includes, for example, methyl, ethyl, 1-propyl, 2-propyl, 2-methyl-1-propyl, 2-methyl-2-propyl, 1-butyl, 2-butyl, 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl, and 2,3-dimethyl-2-butyl groups.

Among these groups, a methyl group or an ethyl group is preferable, and an ethyl group is further preferable.

Any solvent that does not inhibit the bromination reaction may be used as the aforementioned solvent, and such a solvent includes, for example:

water or water-soluble lower alcohols such as methanol, ethanol, and propanol;

ethers such as dioxane, 1,2-dimethoxyethane, and tetrahydrofuran;

halogenated solvents such as methylene chloride, chloroform, carbon tetrachloride, and 1,2-dichloroethane;

lower fatty acids such as acetic acid and trifluoroacetic acid;

organic solvents such as acetonitrile, carbon disulfide, dimethylformamide, and dimethylsulfoxide; and inorganic acids and their aqueous solutions such as sulfuric acid, aqueous solution of sulfuric acid, and aqueous solution of hydrohalic acid. Among these, acetic acid is preferable as a solvent.

These solvents can be used alone or as a combination of multiple solvents.

The aforementioned brominating reagent includes bromine ($Br_2$), 1,3-dibromo-5,5-dimethylhydantoin, N-bromocaprolactam, N-bromosuccinimide, phenyltrimethylammonium tribromide, pyridinium bromide perbromide, and pyrrolidone hydrotribromide. Among these, bromine or N-bromosuccinimide is preferable, and bromine is further preferable.

The molar ratio of the brominating reagent used to the compound of the general formula (I) is preferably 1.0 to 10, more preferably 1.1 to 3.0, and further preferably 1.1 to 1.5.

The reaction temperature is preferably 0° C. to 100° C. The reaction time is preferably six to 24 hours and more preferably ten to 20 hours.

Using Step 1 as above, compounds that have been dibrominated at desired positions can be obtained with a high regioselectivity and a high yield.

Step 2

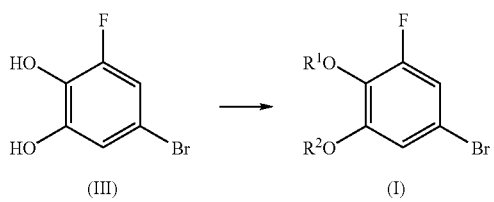

Compounds (I), which are the starting compounds in the above Step 1, can be obtained by reacting, in a solvent, compounds (III) having the above general formula (III) with an alkylating reagent in the presence of a base (Step 2).

The alkylating reagent includes alkyl halides such as $R^1X$ or $R^2X$ (X represents a halogen atom such as an iodine atom, a bromine atom, or a chlorine atom. $R^1$ and $R^2$ have the same meaning as above).

Among these, alkyl halides are preferable, and alkyl iodides are preferable among alkyl halides. The alkylating reagent used is preferably methyl iodide or ethyl iodide, and more preferably ethyl iodide.

The aforementioned base is preferably sodium carbonate, sodium hydrogen carbonate, potassium carbonate, cesium carbonate, sodium methoxide, sodium ethoxide, potassium tert-butoxide, sodium tert-butoxide, and sodium hydride, and more preferably potassium carbonate.

For alkylation, any solvent that does not inhibit the reaction may be used. For example, ethers such as tetrahydrofuran, amides such as N,N-dimethylformamide (DMF), ketones such as acetone, nitriles such as acetonitrile, and halogenated solvents such as methylene chloride can be used.

These solvents can be used alone or as a combination of two or more solvents.

The aforementioned alkylating reagent is preferably used in an amount of not less than two equivalents and more preferably about two to six equivalents of the aforementioned compound (III).

The aforementioned base is preferably used in an amount of not less than two equivalents and more preferably about two to four equivalents of the aforementioned compound (III).

The alkylation reaction temperature is preferably 0° C. to 100° C. The reaction time is preferably about twelve to 24 hours.

Step 3

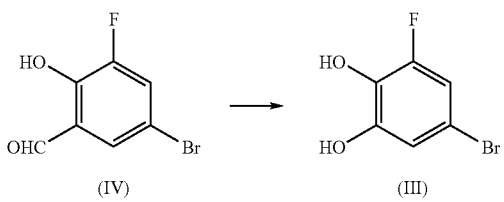

Compounds (III), which are the starting compounds in the above Step 2, can be obtained by reacting, in a solvent, compounds (IV) having the above formula (IV) with a peracid in the presence of a base (Step 3).

The aforementioned peracid includes peracetic acid, hydrogen peroxide solution, and m-chloroperbenzoic acid. Among these, hydrogen peroxide solution is preferable.

The aforementioned peracid is preferably used in an amount of one to three equivalents of compound (IV).

As a base, for example, sodium carbonate, barium hydroxide, lithium hydroxide, sodium hydroxide, potassium hydroxide, and cesium hydroxide can be used. In this case, the base is preferably used in an amount of one to two equivalents of compound (IV).

As a reaction solvent, for example, ethers such as diethylether and tetrahydrofuran, nitriles such as acetonitrile, alcohols such as tert-butylalcohol, or water can be used. These solvents can be used alone or as a combination of multiple solvents.

The reaction temperature is preferably 0° C. to 100° C. The reaction time is preferably about 30 minutes to 24 hours.

Step 4

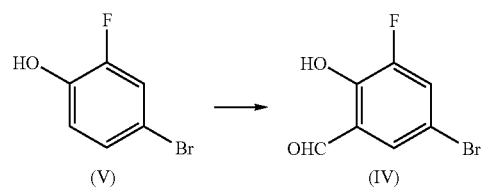

Compounds (IV), which are the starting compounds in the above Step 3, can be obtained by reacting, in a solvent, compounds (V) having the above formula (V) with hexamethylenetetramine (Step 4).

Hexamethylenetetramine is preferably used in an amount of one to five equivalents of compound (V).

For formylation using hexamethylenetetramine, trifluoroacetic acid (TFA), acetic acid, or the like are preferable as solvent, and trifluoroacetic acid is more preferable.

The reaction temperature is preferably 0° C. to 150° C. The reaction time is preferably about 30 minutes to 24 hours.

Methods for producing the dibromofluorobenzene derivatives (compounds (II)) of the present invention comprise any one of the following:

(1) the above Step 1;

(2) the above Steps 1 and 2;

(3) the above Steps 1, 2, and 3; or (4) the above Steps 1, 2, 3, and 4.

These Steps 1 to 4 all have high reaction yields and dibromo products that have been brominated at desired positions can be obtained with a high regioselectivity, particularly by using compounds that have bromo groups introduced at specific positions as starting compounds. In addition, the starting compounds (V) are easily available, and complicated purification steps are not needed in each step. Therefore, the production methods of the present invention are also industrially superior.

The following compounds (I) and (III) of the present invention are novel compounds.

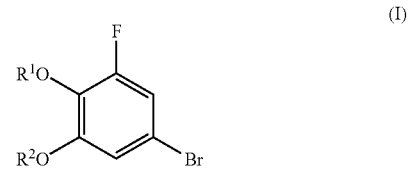

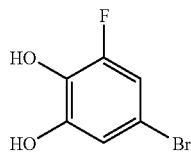

(III)

In the above formula, $R^1$ and $R^2$ each independently represent a $C_{1-6}$ alkyl group. As $C_{1-6}$ alkyl group, $R^1$ and $R^2$ are preferably both a $C_{1-3}$ alkyl group, more preferably both a methyl or ethyl group, and particularly preferably both an ethyl group.

Moreover, the aforementioned compounds (III) may be compounds having the following general formula (III-1), which have hydroxy groups protected with $R^a$ and $R^b$.

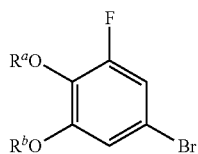

(III-1)

In the above formula, $R^a$ and $R^b$ each independently represent a hydroxy protecting group, or $R^a$ and $R^b$ together represent a protecting group.

However, the case where $R^a$ is a methyl group and $R^b$ is a t-butyldiphenylsilyl group is excluded.

The hydroxy protecting groups $R^a$ and $R^b$ are not particularly limited, and any groups that are generally used as hydroxy protecting groups can be used without particular limitations.

For such hydroxy protecting groups, those that are listed in, for example, Protective Groups in Organic Synthesis, Theodora W. Greene, Peter G. M. Wuts (Third Edition, John Wiley & Sons, Inc.) can be used.

Specifically, they include, for example, an alkylsilyl group such as trimethylsilyl, triethylsilyl, isopropyldimethylsilyl, t-butyldimethylsilyl, methyldiisopropylsilyl, methyldi-t-butylsilyl, triisopropylsilyl, diphenylmethylsilyl, diphenylbutylsilyl, diphenylisopropylsilyl, or phenyldiisopropylsilyl group;

a $C_{1-6}$ alkylcarbonyl group such as acetyl or propionyl group;

a $C_{1-6}$ alkyloxycarbonyl group such as methoxycarbonyl, ethoxycarbonyl, or t-butoxycarbonyl group;

an alkoxymethyl group such as methoxymethyl or ethoxymethyl group;

an alkoxylated alkoxymethyl group such as 2-methoxyethoxymethyl group;

an alkoxyethyl group such as 1-ethoxyethyl group; and a substituted benzyl group such as benzyl, 4-methylbenzyl, 4-methoxybenzyl, or o-nitrobenzyl group.

Additionally included are phenylcarbonyl, tetrahydrofuranyl, tetrahydropyranyl, benzyloxymethyl, and formyl groups.

Among these groups, a preferable hydroxy protecting group is an alkylsilyl group or a substituted benzyl group, and further preferably a t-butyldimethylsilyl group or a benzyl group.

In the case where $R^a$ and $R^b$ together represent a protecting group, $R^a$ and $R_b$, for example, may be combined together with the two oxygen atoms attached to the benzene ring to form an alkylenedioxy group.

Herein, the term "alkylenedioxy group" is a divalent group represented by —O—R—O— (where R is an alkylene group of preferably one to six carbon atoms, and more preferably of one to four carbon atoms). An alkylenedioxy group includes, for example, methylenedioxy, ethylenedioxy, trimethylenedioxy, tetramethylenedioxy, —O—CH(CH$_3$)—O—, and —O—C(CH$_3$)$_2$—O—.

The protecting groups described above can be introduced and removed using conventional procedures.

These compounds having the aforementioned general formulae (I) to (III-1) are useful as intermediates when producing 2-iminopyrrolidine derivatives that are useful as thrombin receptor antagonists (Patent Document 1), for example, compounds having the following formula (A1):

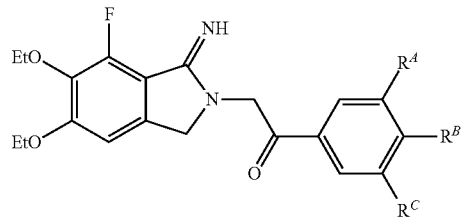

(A1)

(wherein $R^A$ represents a $C_{1-6}$ alkyl group, $R^B$ represents a $C_{1-6}$ alkoxy group, and $R^C$ represents a 5-14 membered heterocyclic group) or salts thereof.

All prior art references cited herein are incorporated by reference into this description.

EXAMPLES

Herein below, the present invention will be specifically described with reference to Examples, but it is not to be construed as being limited thereto. In the present description, room temperature refers to a temperature within the range of 20° C. to 30° C., and preferably refers to a temperature of about 25° C.

Example 1

5-Bromo-3-fluoro-2-hydroxybenzaldehyde

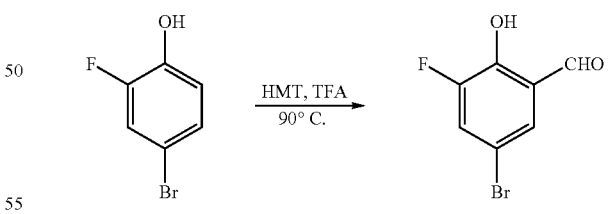

To a solution of 4-bromo-2-fluorophenol (100 g, 0.52 mol) in trifluoroacetic acid (TFA) (400 mL), hexamethylenetetramine (HMT) (146.8 g, 1.05 mol) was added under a nitrogen atmosphere in three portions over 20 minutes, the mixture was stirred at room temperature for 20 minutes, and then at 90° C. for 13 hours, and then cooled to room temperature. Water (600 mL) and a 50% aqueous solution of sulfuric acid (300 ML) were sequentially added thereto at room temperature, and the mixture was stirred at room temperature for two hours. The resultant mixture was extracted three times with ethyl acetate (1 L), the organic layer was washed four times with 1 N aqueous solution of hydrochloric acid (1 L), twice with saturated saline, and dried over anhydrous magnesium sulfate. The solvent was distilled off from the organic layer under reduced pressure and the residue was azeotroped twice with toluene. Ethanol (20 mL) was added to the residue, and the solid obtained after filtration of the suspended solution was washed twice with ethanol (10 mL) to give 49.6 g of the title compound (yield: 43%).

Example 2

5-Bromo-3-fluorobenzene-1,2-diol

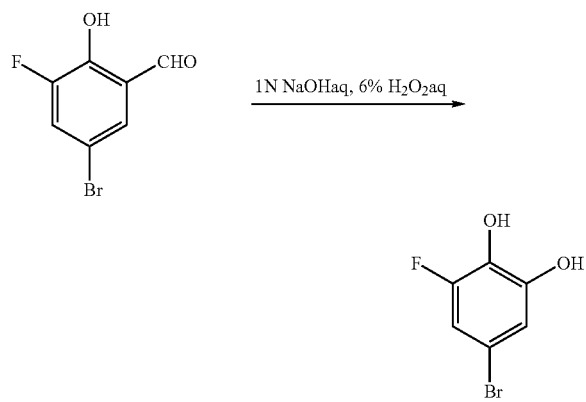

To a 1 N aqueous solution of sodium hydroxide (230 mL, 0.23 mol), 5-bromo-3-fluoro-2-hydroxybenzaldehyde (45.0 g, 0.21 mol) was added at room temperature, and a 6% hydrogen peroxide solution (225 mL) was added dropwise over five minutes at room temperature. After the reaction mixture was stirred at room temperature for two hours, a saturated aqueous solution of sodium thiosulfate (150 mL) was added thereto at room temperature. The mixture was extracted three times with ethyl acetate (450 mL), the organic layer was washed sequentially with a 1 N aqueous solution of hydrochloric acid (150 mL) and saturated saline, dried over anhydrous magnesium sulfate, and filtered through silica gel. The solvent was distilled off from the resultant filtrate under reduced pressure to give 39.0 g of the title compound (yield: 92%).

$^1$H-NMR(400 MHz, CDCl$_3$) δ: 6.89 (1H, dd, J=2, 2 Hz), 6.85 (1H, dd, J=9, 2 Hz).

Example 3

5-Bromo-1,2-diethoxy-3-fluorobenzene

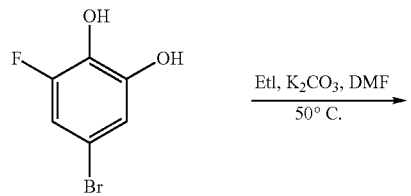

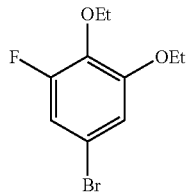

To a solution of 5-bromo-3-fluorobenzene-1,2-diol (37.5 g, 0.18 mol) in N,N-dimethylformamide (DMF) (375 mL), ethyl iodide (58.0 mL, 0.72 mol) and potassium carbonate (62.6 g, 0.45 mol) were added sequentially under a nitrogen atmosphere, the mixture was stirred at room temperature for 30 minutes, and then stirred at 50° C. for 16.5 hours. The reaction mixture was cooled to room temperature and water (1.0 L) was added thereto. The mixture was extracted once with ethyl acetate (1.0 L) and twice with ethyl acetate (500 mL). Water (1.0 L) was added to the organic layer and the mixture was filtered through celite. After separating the filtrate, the organic layer was washed sequentially with water (1.0 L), twice with a 5 N aqueous solution of sodium hydroxide (200 mL), and saturated saline. The organic layer was dried over anhydrous magnesium sulfate and the solvent was distilled off under reduced pressure. The resultant residue was purified by silica gel column chromatography (hexane, ethyl acetate) to give 41.7 g of the title compound (yield: 87%).

$^1$H-NMR(400 MHz, CDCl$_3$) δ: 6.88 (1H, dd, J=10, 2 Hz), 6.81 (1H, dd, J=2, 2 Hz), 4.10 (2H, q, J=7 Hz), 4.05 (2H, q, J=7 Hz), 1.44 (3H, t, J=7 Hz), 1.35 (3H, t, J=7 Hz).

Example 4

1,2-Dibromo-4,5-diethoxy-3-fluorobenzene

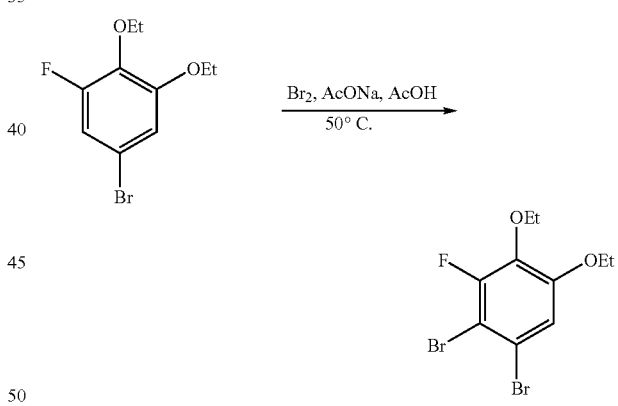

To a solution of 5-bromo-1,2-diethoxy-3-fluorobenzene (40.0 g, 0.15 mol) in acetic acid (200 mL), sodium acetate (16.2 g, 0.20 mol) and bromine (31.6 g, 0.20 mol) were added sequentially at room temperature, and the mixture was stirred at 50° C. for 1.5 hours. The reaction mixture was cooled to room temperature, and a saturated aqueous solution of sodium thiosulfate (400 mL) and water (400 mL) were added sequentially. The mixture was extracted once with heptane (800 mL) and three times with heptane (400 mL). The organic layer was washed sequentially with water (400 mL), once with a 2 N aqueous solution of sodium hydroxide (200 mL), once with a 2 N aqueous solution of sodium hydroxide (100 mL), and water (400 mL), then dried over anhydrous magnesium sulfate. The solvent was distilled off from the organic layer under reduced pressure and the residue was filtered. The filtrate was then purified by silica gel column chromatography (hexane, ethyl acetate) to give 52.0 g of the title compound (yield:quant.).

INDUSTRIAL APPLICABILITY

As described above, the present invention allows compounds (II) to be synthesized with a good yield by using the aforementioned compounds (I), compounds (III), compounds (IV), and compounds (V) as intermediates. Namely, by using compounds that have bromo groups introduced at specific positions as starting compounds, dibromo products that have been brominated at desired positions can be obtained with a higher regioselectivity compared to conventional methods (described in WO 02/85855).

The compounds of interest can be obtained quickly and easily, because the starting compounds (V) are easily available and complicated purification steps are not needed in each step. Therefore, the present production methods are industrially superior compared to conventional methods (described in WO 02/85855).

The invention claimed is:

1. A method for producing a dibromofluorobenzene derivative (compound (II)) having the following general formula (II):

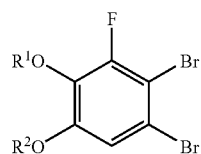
(II)

(wherein $R^1$ and $R^2$ each independently represent a $C_{1-6}$ alkyl group), wherein the method comprises the step of reacting, in a solvent, a compound (I) having the following general formula (I):

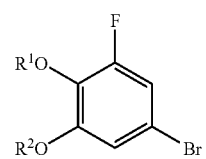
(I)

(wherein $R^1$ and $R^2$ each have the same meaning as $R^1$ and $R^2$ in the aforementioned formula (II)) with a brominating reagent (Step 1), such that bromination selectively occurs at position 4 of compound (I);
the method further comprising a step of reacting, in a solvent, a compound (III) having the following formula (III):

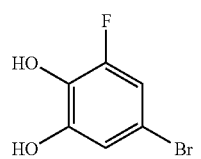
(III)

with an alkylating agent in the presence of a base to obtain the aforementioned compound (I)
(Step 2).

2. The method of claim 1, wherein the brominating reagent is bromine.

3. The method of claim 1, wherein the alkylating agent is an alkyl halide.

4. The method of claim 1, further comprising a step of reacting, in a solvent, a compound (IV) having the following formula (IV):

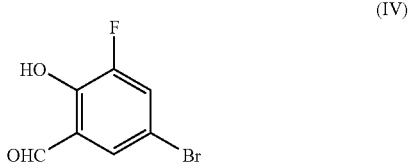
(IV)

with a peracid in the presence of a base to obtain the aforementioned compound (III) having the following formula (III):

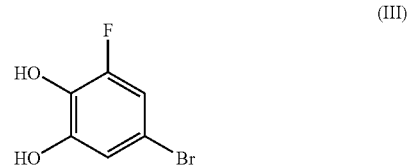
(III)

(Step 3).

5. The method of claim 4, wherein the peracid is a hydrogen peroxide solution.

6. The method of claim 4, further comprising a step of reacting, in a solvent, a compound (V) having the following formula (V):

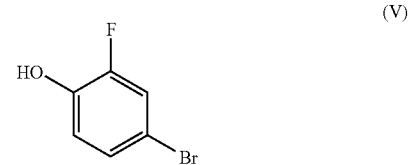
(V)

with hexamethylenetetramine to obtain the aforementioned compound (IV) having the following formula (IV):

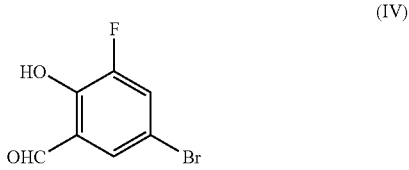
(IV)

(Step 4).

7. The method of claim 1, wherein $R^1$ and $R^2$ in the aforementioned general formulae (I) and (II) are both an ethyl group.

* * * * *